United States Patent [19]

Croce et al.

[11] 4,145,228

[45] Mar. 20, 1979

[54] PROCESS FOR THE JOINT PRODUCTION OF AROMATIC AMINES AND IRON OXIDE PIGMENTS

[75] Inventors: Piero D. Croce, Milan; Tullio Pellizzon, Paderno Dugnano (Milan); Peter Schwarz; Luigi Piccolo, both of Milan, all of Italy

[73] Assignee: Euteco S.p.A., Milan, Italy

[21] Appl. No.: 852,264

[22] Filed: Nov. 17, 1977

[30] Foreign Application Priority Data

Nov. 19, 1976 [IT] Italy ............................... 29541 A/76

[51] Int. Cl.$^2$ .............................................. C09C 1/24
[52] U.S. Cl. ..................................... 106/304; 423/632; 423/633; 423/634; 260/580
[58] Field of Search ................ 106/304; 423/632, 633, 423/634; 260/575, 580

[56] References Cited

U.S. PATENT DOCUMENTS

| 1,793,941 | 2/1931 | Laux ..................................... 260/580 |
| 1,849,428 | 3/1932 | Laux ..................................... 260/580 |
| 2,866,686 | 12/1958 | Bennetch ............................. 423/633 |
| 3,619,137 | 11/1971 | Ratcliffe ............................... 423/633 |

Primary Examiner—Winston A. Douglas
Assistant Examiner—J. V. Howard
Attorney, Agent, or Firm—Sughrue, Rothwell, Mion, Zinn and Macpeak

[57] ABSTRACT

Aromatic amines and iron oxide pigment are produced by reacting a ferrous salt, a reduceable aromatic nitrogen compound chosen from nitroderivatives with a single nitro-group or with two nitro-groups and azoderivatives, and a basic compound, chosen from hydroxides and carbonates of ammonium, alkali metals and alkaline earth metals, operating at 25°–200° C. in an aqueous medium. The color of the pigment can be varied from yellow to black by increasing the reaction temperature and the molar ratio between ferrous salt and aromatic nitrogen compound.

17 Claims, No Drawings

PROCESS FOR THE JOINT PRODUCTION OF AROMATIC AMINES AND IRON OXIDE PIGMENTS

The present invention relates to a process for the joint production of aromatic amines and iron oxide pigments.

In particular the present invention relates to a process for the joint production of iron oxide pigments and aromatic amines by reduction of the corresponding reduceable aromatic nitrogen compounds with a ferrous salt.

The reduction of reduceable aromatic nitrogen compounds with metallic iron in an acid medium for the production of aromatic amines and of a precipitate of iron oxides with pigmentary characteristics is already known in the art.

This process presents some non-negligible drawbacks, dependent above all on problems of corrosion and erosion of the installations due to the both chemical and mechanical aggressiveness of the solutions and suspensions used.

The reduction of reduceable aromatic nitrogen compounds with iron compounds for the production of aromatic amines is also known in the art. In this case it has not been possible until now to find the conditions for simultaneously obtaining precipitates of iron oxides with satisfactory pigmentary characteristics, variable at will within a wide range of desired colours.

We have not found a process which by reduction with ferrous salts of reduceable aromatic nitrogen compounds, as well as acheiving high yields in the production of the corresponding amines, also allows pigmentary iron oxides to be obtained with a colour variable at will within a wide range.

Thus, the invention provides a process for the joint production of aromatic amines and iron oxide pigments, which comprises bringing into contact a ferrous salt, a reduceable aromatic nitrogen compound chosen from aromatic nitroderivatives with a single nitro-group or two nitro-groups and aromatic azoderivatives, and a basic compound chosen from hydroxides and carbonates of alkali metals, alkaline earth metals and ammonium, reacting said nitrogen compound, ferrous salt and basic compound in an aqueous medium at a temperature of from 25° to 200° C. with a molar ratio between ferrous salt and aromatic nitrogen compound of from 3:1 to 15:1 in the case (a) of a nitroderivative with a single nitro-group, from 6:1 to 30:1 in the case (b) of a nitroderivative with two nitro-groups, and from 2:1 to 10:1 in the case (c) of an azoderivative, and with a molar ratio between basic compound and ferrous salt of from 1.8:1 to 3:1 in the case of a basic compound with a monovalent cation and from 0.9:1 to 1.5:1 in the case of a basic compound with a divalent cation, and recovering the amine and iron oxide pigment thus obtained from the reaction products.

The reaction is generally carried out for a period of from 30 minutes to 12 hours.

The reagents may be brought into contact in any order. Advantageously the reagents may be brought into contact by mixing an aqueous solution of the ferrous salt with the reduceable aromatic nitrogen compound and then gradually adding an aqueous solution of the basic compound to the resulting mixture.

Again advantageously at least a portion of the basic compound may first be added in the form of an aqueous solution to the aqueous solution of ferrous salt to convert at least a part of this salt into ferrous hydroxide precipitate and the aromatic nitrogen compound and the residual portion of the basic compound are then fed into the resulting slurry.

Preferably the feeding of the aqueous solution of the basic compound is carried out gradually over a period of from 3 to 120 minutes. The best results are obtained with feeding times of from 20 to 70 minutes.

The said alkaline earth metal is preferably magnesium. The basic compound is preferably sodium or ammonium hydroxide.

The ferrous salt is preferably ferrous sulphate.

A particularly advantageous characteristic of the process of the present invention consists in the possibility of using waste ferrous sulphate heptahydrate obtained from titaniferous solutions produced in the process for the production of titanium dioxide by the sulphate method.

In this case the aromatic nitrogen compound is transformed into the corresponding amine, the iron in the ferrous sulphate is converted into iron oxide while the cation of the basic compound combines with the sulphate ion giving the corresponding sulphate.

With the process of this invention it is therefore possible to obtain three useful and valuable products (amines, iron oxides, and sulphates of alkali metals, ammonium or alkaline earth metals) starting from a waste material, the disposal of which presents great ecological inconveniences and the conversion of which is always desirable, above all into products which can be usefully employed.

The aromatic nitrogen compounds may be chosen from compounds having the following general formulae:

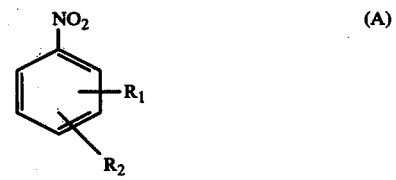

(A)

where $R_1$ and $R_2$ independently are hydrogen, an alkyl radical, a halogen, OH, OCH$_3$, NH$_2$, CHO, COOH, SO$_2$OH or SO$_2$NH$_2$;

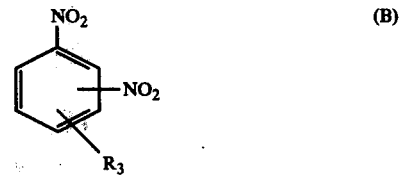

(B)

where $R_3$ is hydrogen or an alkyl radical;

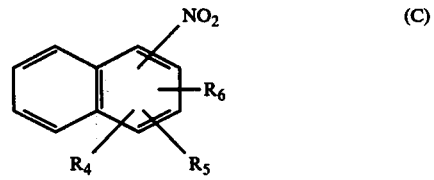

(C)

where $R_4$, $R_5$ and $R_6$ independently are H, NH$_2$, OH, a halogen or SO$_2$OH;

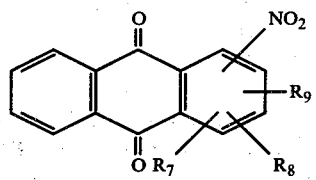

where $R_7$, $R_8$ and $R_9$ independently are H, $SO_2OH$ or a halogen; and

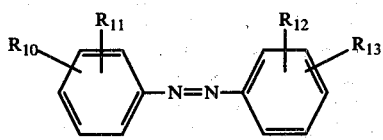

where $R_{10}$, $R_{11}$, $R_{12}$ and $R_{13}$ independently are H, $NH_2$, OH, a halogen or $SO_2OH$.

The separation of the reaction products can be carried out by conventional methods.

The amines are separated by various methods according to their chemico-physical characteristics. For example they can be separated by steam distillation, or by the crystallization of one of their salts or by solvent extraction.

The iron oxides may be separated by filtration or centrifuging. To improve the pigmentary characteristics of the iron oxides the latter are conveniently subjected to a series of washings, for example with acidulated water, and to a final drying.

The sulphate, preferably of an alkali metal, magnesium or ammonium, is conveniently recovered from the residual solution after the separation of the iron oxide and of the amine, through crystallization by cooling.

By operating according to the process of the present invention iron oxides are obtained with colours which go from yellow to red to brown to black according to the conditions employed.

In particular the colours depend mainly on the molar ratio of the ferrous salt to the reduceable aromatic nitrogen compound, but the temperature of the reaction may also have a certain influence.

Thus by operating at a temperature of from 30° to 65° C. and with a molar ratio of the ferrous salt to the aromatic nitrogen compound between 3:1 and 3.8:1 iron oxides with yellow colours are obtained; operating instead at a temperature of from 60° to 105° C. and with a molar ratio of the ferrous salt to the organic nitrogen compound between 3.8:1 and 5.5:1 iron oxides with red colours are obtained; operating at a temperature of from 90° to 105° C. and with a molar ratio of the ferrous salt to the organic nitrogen compound between 5.5:1 and 7:1 iron oxides with brown colours are obtained, while there is a progressive shifting towards dark brown colourings when said ratio is greater than 7:1 and up to 10:1; lastly by operating with a temperature still from 90° to 105° C. but with a molar ratio of the ferrous salt to the aromatic nitrogen compound between 10:1 and 15:1 iron oxides with colours from dark grey to black are obtained.

The ratios between the ferrous sulphate and the aromatic nitrogen compound recorded above, are for simplicity, referred to the nitro-derivates with a single reduceable nitro-group. It is understood that in the case of compounds with two reduceable nitro-groups the ratios must be considered to be multiplied by 2 and in the case of azoderivates by $\frac{3}{2}$.

Without wishing to engage in any theory this is probably due to the fact that the conditions indicated have a preponderant influence on the chemical nature, and above all the degree of oxidation of the iron oxide, said degree of oxidation being the main factor responsible for the various colourings.

The process of the present invention besides allowing the conversion of a waste product into three useful and valuable products (amines, iron oxide pigments and sulphates) and allowing pigments to be obtained with colours variable at will within a wide range according to the conditions imposed, also has the further advantage that it can be carried out in technically simple and economical plants. The working conditions do not lead to the problems of corrosion and erosion of the installations and the problems due to difficulties in filtration and to the burden and length of the operations, which are normally encountered in commercial processes for the production of iron oxide pigments.

The invention will now be illustrated by the following examples which do not in any way limit its scope.

EXAMPLE 1

130 grams of waste ferrous sulphate obtained in the process for the production of titanium dioxide from ilmenite by the sulphate method, having the following composition by weight: $FeSO_4.7H_2O$ 88.5%; $MgSO_4.7H_2O$ 6.3%; $Al_2(SO_4)_3.18H_2O$ 0.3%; $TiOSO_4$ 0.18%; $MnSO_4.5H_2O$ 0.3%; free $H_2SO_4$ 0.5%; $CaSO_4.2H_2O$ 0.2%; $Cr_2(SO_4)_3$ 2 ppm; $VOSO_4$ 50ppm; free $H_2O$ 3.5%; (corresponding to 0.41 moles of ferrous sulphate heptahydrate) were added to 50 ml of water.

This mixture was used in a series of tests, adding to the mixture of 0.05 moles respectively of nitrobenzene, p-nitrotoluene, o-nitrotoluene, p-chloronitrobenzene and o-chloronitrobenzene.

The resulting mixture was then preheated each time up to a temperature of 90° C. in a reflux distillation flask in an inert atmosphere.

To the mixture was then added over 30 minutes and under agitation one mole of NaOH in the form of a 44 wt.% aqueous solution. After the addition the reaction was completed in 2.5 hours, the mixture being maintained at a temperature of from 98° to 102° C. and under agitation.

The mass obtained was then submitted to steam distillation; the cooled distillate, after addition of 20 grams of sodium chloride, was extracted twice with 20ml of $CH_2Cl_2$.

The amine corresponding to the nitroderivative used was recovered from the organic phase by removing the solvent by evaporation and drying the evaporation residue.

In the case of nitrobenzene aniline was obtained with a yield of 92%.

In the case of p-nitrotoluene, o-nitrotoluene, p-chloronitrobenzene and o-chloronitrobenzene the yields were respectively 88%, 90%, 86% and 84%.

The residue from the steam distillation was filtered while hot in order to separate the iron oxide precipitate from the sodium sulphate solution.

This precipitate was washed with a 2% solution of sulphuric acid, filtered, washed with water and then dried. This product (in a quantity of from about 29 to 32 grams according to the nitroderivate used) was found in all cases to be formed of dark brown pigments of a practically identical shade.

The residual solution containing sodium sulphate was then treated with 2 grams of Celite (Registered Trade Mark), filtered and cooled.

The precipitate thus obtained was filtered off and dried under vacuum at 80° C.

In all the five cases considered (nitrobenzene, p-nitrotoluene, o-nitrotoluene, p-chloronitrobenzene and o-chloronitrobenzene) products with a purity greater than 98% were obtained.

EXAMPLE 2

79.1 grams of waste ferrous sulphate of the same type as in Example 1 (corresponding to 0.25 moles of $FeSO_4.7H_2O$) were dissolved in water to give a 17.5% solution by weight of $FeSO_4.7H_2O$. 0.58 moles of nitrobenzene were added to this solution and the mixture was preheated in a reflux distillation flask at about 100° C. 0.525 moles of NaOH in the form of a 20 wt.% aqueous solution were added to the mixture in two hours and under agitation. After the addition the reaction was completed in 2 hours, the mixture being maintained at a temperature of 100° C. under agitation.

The reaction products were then separated under the same conditions as in Example 1, a red coloured pigment being obtained. Microphotographs of the pigment show that the latter has a uniform grain size (about 0.20–0.25 $\mu$).

EXAMPLE 3

0.04 moles of nitrobenzene were added to the ferrous sulphate solution of Example 2 and the mixture was heated in a reflux distillation flask at about 100° C. 0.525 moles of NaOH in a 20% by weight aqueous solution were then added under agitation over a time of 50 minutes, the temperature being maintained between 98° and 102° C. The reaction was completed in 2 hours, the temperature being maintained within the range stated above and the mixture being kept under agitation.

The reaction products were separated according to the procedure of Example 1, a pigment which is brown in colour being obtained.

EXAMPLE 4

0.019 moles of nitrobenzene were added to the ferrous sulphate solution of Example 2 and the mixture was heated in a reflux distillation flask at about 100° C. 0.525 moles of NaOH in a 20% by weight aqueous solution were then added under agitation over a period of 50 minutes.

The reaction was completed in 2 hours, the temperature being maintained at 98°–102° C. and the mixture being kept under agitation. The reaction products were then separated according to the procedure shown in Example 1, a pigment which is black in colour being obtained.

EXAMPLE 5

79.1 grams of waste ferrous sulphate heptahydrate of the same type as in Example 1 (0.25 moles of ferrous sulphate) were dissolved in water to give a 15% by weight solution of $FeSO_4.7H_2O$.

To this solution preheated to 60° C., were added under agitation, 0.479 moles of NaOH in a 7 wt.% aqueous solution, over 25 minutes, and subsequently 0.08 moles of nitrobenzene over 10 minutes.

0.46 moles of NaOH in a 7 wt.% aqueous solution were then added under agitation over a period of 3 hours, the mixture being maintained at a temperature of 60° C. The reaction was completed in 5 hours, the temperature being maintained at 60° C. and the mixture being kept under agitation.

The reaction products were then separated according to the procedure shown in Example 1, a pigment which is yellow in colour with shades tending towards green being obtained.

EXAMPLE 6

130 grams of waste ferrous sulphate heptahydrate of the same type as in Example 1 (0.41 moles of ferrous sulphate) were added to 75 ml of water. To this mixture were added in two different tests 0.05 moles of 2,4-dimethylnitrobenzene and of o-nitroanisole respectively.

The mixtures obtained in the two cases were then preheated to 95° C. in a reflux distillation flask and one mole of NaOH in a 35 wt.% aqueous solution was added to each mixture under agitation over 60 minutes.

The reaction was then completed, the mixture being kept at a temperature of between 95° and 100° C. for 3 hours.

The reaction products were recovered operating as shown in Example 1, 2,4-dimethylaniline and o-methoxyaniline being obtained respectively with a yield of 84 and 83% respectively.

In both cases a dark brown pigment of practically identical shade was obtained.

EXAMPLE 7

In four different tests 0.05 moles of p-nitrobenzoic acid, p-nitrophenol, m-nitrobenzenesulphonic acid and p-nitroaniline respectively were added to the mixture of ferrous sulphate and water of Example 6.

The mixtures obtained in the four cases were preheated to 90° C. in a reflux distillation flask in an inert atmosphere and then 1.1 moles of $NH_4OH$ in the form of an aqueous solution containing 26% by weigh of $NH_3$ were added in each case under agitation over a period of 60 minutes.

The reaction was completed in 3 hours, the mixture being maintained at a temperature of between 95 and 100° C.

The iron oxide precipitate was filtered off at elevated temperature and the amine was recovered by acidification of the residual solution to a pH = 5.5 in the cases of p-aminobenzoic acid, m-aminobenzenesulphonic acid and of the p-aminophenol while the p-phenylenediamine was recovered by cooling and filtration.

The yields of p-aminobenzoic acid, p-aminophenol, m-aminobenzenesulphonic acid and p-phenylenediamine were 75, 77, 60 and 70% respectively.

In all cases a dark brown pigment of practically identical shade was obtained.

EXAMPLE 8

0.025 moles of m-dinitrobenzene and 2,4-dinitrotoluene respectively were added to the mixture of ferrous sulphate and water of Example 6 in two different tests. The mixtures were preheated to 95° C. in a reflux distillation flask in an inert atmosphere and 1.2 moles of $NH_4OH$ in the form of an aqueous solution containing 26% by weight of $NH_3$ were added in each case under agitation over a period of 60 minutes.

The reaction was completed, the mixture being kept at a temperature of between 95° and 100° C. for 3 hours.

The iron oxide precipitate was filtered off at elevated temperature, while the m-phenylenediamine was recovered by extraction with $CH_2Cl_2$ and the 2,4-diaminotoluene was recovered by crystallization by cooling.

The yield of m-phenylenediamine was equal to 50%, while that of the 2,4-diaminotoluene was equal to 75%.

In each case a dark brown pigment of practically identical shade was obtained.

EXAMPLE 9

To the mixture of ferrous sulphate and water of Example 6 was added 0.05 moles of p-aminoazobenzene.

The mixture was then preheated to 95° C. in a reflux distillation flask in an inert atmosphere and then 1.2 moles of $NH_4OH$ in a 26% by weight aqueous solution of $NH_3$ were added under agitation over a period of 60 minutes. The reaction was then completed, the mixture being kept at a temperature of between 95° and 100° C. for 3 hours.

The iron oxide precipitate was filtered off at elevated temperature, while the p-phenylenediamine was recovered from the filtrate by crystallization by cooling. The yield of p-phenylenediamine was equal to 90% while the iron oxide precipitate was dark brown in colour.

EXAMPLE 10

Example 2 was repeated, the waste ferrous sulphate heptahydrate obtained as a byproduct in the preparation of titanium dioxide by the sulphate method being substituted by pure ferrous sulphate heptahydrate having a titre greater than 99%.

For this purpose 70g of pure ferrous sulphate heptahydrate (0.25 moles) were dissolved in water to give a 17.5% solution by weight of $FeSO_4.7H_2O$.

This solution was then treated under the same conditions as in Example 2, thus obtaining aniline with a yield of 93%, and a pigment red in colour and of a shade practically identical to that of Example 2.

EXAMPLE 11

To the mixture of ferrous sulphate and water of Example 6 was added 0.05 moles of p-nitroaniline and the mixture obtained was loaded into an autoclave furnished with an agitator, and heated at 155° C. at an autogenous pressure of 5 atmospheres. While keeping the temperature at this value 1.2 moles of $NH_4OH$ as an aqueous solution containing 26 wt.% of $NH_3$ were introduced over a period of 3 minutes. After a further 30 minutes the reaction mixture was extracted from the autoclave and cooled.

The separation of the reaction products was then carried out according to the procedure of Example 7. The yield of p-phenylene-diamine was 76%, while the iron oxide precipitate was dark brown in colour.

We claim:

1. A process for the joint production of aromatic amines and iron oxide pigments, which comprises bringing into contact a ferrous salt, a reduceable aromatic nitrogen compound selected from the group consisting of aromatic nitroderivatives with a single nitro-group or two nitro-groups and aromatic azoderivatives, and a basic compound selected from the group consisting of hydroxides and carbonates of alkali metals, alkaline earth metals and ammonium, reacting said nitrogen compound, ferrous salt and basic compound in an aqueous medium at a temperature of from 25° to 200° C. with a molar ratio between ferrous salt and aromatic nitrogen compound of from 3:1 to 15:1 in the case (a) of a nitroderivative with a single nitro-group, from 6:1 to 30:1 in the case (b) of a nitroderivative with two nitro-groups, and from 2:1 to 10:1 in the case (c) of an azoderivative, and with a molar ratio between basic compound and ferrous salt of from 1.8:1 to 3:1 in the case of a basic compound with a monovalent cation and from 0.9:1 to 1.5:1 in the case of a basic compound with a divalent cation, and recovering the amine and iron oxide pigment thus obtained from the reaction products.

2. The process of claim 1, in which the reaction is carried out for a period of from 30 minutes to 12 hours.

3. The process of claim 1, wherein said alkaline earth metal is magnesium.

4. The process of claim 1, wherein said basic compound is sodium hydroxide.

5. The process of claim 1, wherein said basic compound is ammonium hydroxide.

6. The process of claim 1, wherein said ferrous salt is ferrous sulphate.

7. The process of claim 1, wherein said ferrous salt is the waste ferrous sulphate heptahydrate obtained from titaniferous solutions produced in the process for preparing titanium dioxide by the sulphate method.

8. The process of claim 1, in which the ferrous salt, the aromatic nitrogen compound and the basic compound are brought into contact by mixing an aqueous solution of the ferrous salt with the aromatic nitrogen compound and gradually adding an aqueous solution of the basic compound to the resulting mixture.

9. The process of claim 8, in which said aqueous solution of basic compound is added over a period of from 3 to 120 minutes.

10. The process of claim 8, in which said aqueous solution of basic compound is added over a period of from 20 to 70 minutes.

11. The process of claim 1, in which the ferrous salt, the aromatic nitrogen compound and the basic compound are brought into contact by adding at least a part of the basic compound in the form of an aqueous solution to an aqueous solution of the ferrous salt, and adding the aromatic nitrogen compound and the remaining part of the basic compound to the resulting slurry.

12. The process of claim 1, in which yellow iron oxide pigment is produced by maintaining the reaction temperature at a value of from 30° to 65° C., the molar ratio between ferrous salt and aromatic nitrogen compound being between 3:1 and 3.8:1 in said case (a), between 6:1 and 7.6:1 in said case (b) and between 2:1 and 2.55:1 in said case (c).

13. The process of claim 1, in which red iron oxide pigment is produced by maintaining the reaction temperature at a value of from 60° to 105° C., the molar ratio between ferrous salt and aromatic nitrogen compound being between 3.8:1 and 5.5:1 in said case (a), between 7.6:1 and 11:1 in said case (b) and between 2.55:1 and 3.7:1 and 3.7:1 in said case (c).

14. The process of claim 1, in which brown iron oxide pigment is produced by maintaining the reaction temperature at a value of from 90° to 105° C., the molar ratio between ferrous salt and aromatic nitrogen compound being between 5.5:1 and 7:1 in said case (a), between 11:1 and 14:1 in said case (b) and between 3.7:1 and 4.75:1 in said case (c).

15. The process of claim 1, in which dark brown iron oxide pigment is produced by maintaining the reaction temperature at a value of from 90° to 105° C., the molar ratio between ferrous salt and aromatic nitrogen compound being between 7:1 and 10:1 in said case (a), between 14:1 and 20:1 in said case (b) and between 4.75:1 and 6.66:1 in said case (c).

16. The process of claim 1, in which iron oxide pigment of from dark grey to black colouring is produced by maintaining the reaction temperature at a value of from 90° to 105° C., the molar ratio between ferrous salt and aromatic nitrogen compound being between 10:1 and Z15:1 in said case (a), between 20:1 and 30:1 in said case (b) and between 6.66:1 and 10:1 in said case (c).

17. A process for the joint production of aromatic amines and iron oxide pigments, which comprises bringing into contact a ferrous salt, a basic compound selected from the group consisting of hydroxides and carbonates of alkali metals, alkaline earth metals, and ammonium, and a reduceable aromatic compound consisting of an aromatic nitroderivative with a single nitro-group or two nitro-groups or an aromatic azoderivative, said reduceable aromatic compound being selected from the following classes:

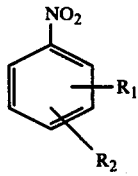

where $R_1$ and $R_2$ independently are H, an alkyl radical, a halogen, OH, $CH_3$, $NH_2$, CHO, COOH, $SO_2H$ or $SO_2NH_2$,

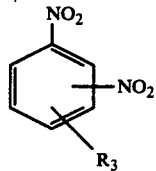

where $R_3$ is hydrogen or an alkyl radical,

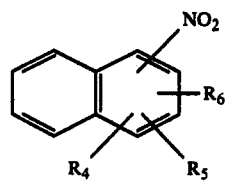

where $R_4$, $R_5$ and $R_6$ independently are H, $NH_2$, OH, a halogen or $SO_2OH$,

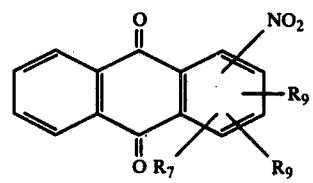

where $R_7$, $R_8$ and $R_9$ independently are H, $SO_2OH$ or a halogen, and

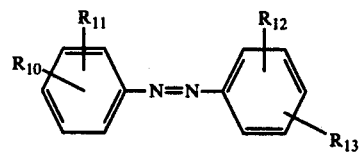

where $R_{10}$, $R_{11}$, $R_{12}$ and $R_{13}$ independently are H, $NH_2$, OH, a halogen or $SO_2CH$, reacting said nitrogen compound, ferrous salt and basic compound in an aqueous medium at a temperature of from 25° to 200° C. with a molar ratio between ferrous salt and aromatic nitrogen compound of from 3:1 to 15:1 in the case (a) of a nitroderivative with a single nitro-group, from 6:1 to 30:1 in the case (b) of a nitroderivative with two nitro-groups, and from 2:1 to 10:1 in the case (c) of an azoderivative, and with a molar ratio between basic compound and ferrous salt of from 1.8:1 to 3:1 in the case of a basic compound with a monovalent cation and from 0.9:1 to 1.5:1 in the case of a basic compound with a divalent cation, and recovering the amine and iron oxide pigment thus obtained from the reaction products.

* * * * *